United States Patent [19]

Brown

[11] Patent Number: 4,643,181
[45] Date of Patent: Feb. 17, 1987

[54] ANTIMICROBIAL DRESSING OR DRAPE MATERIAL

[75] Inventor: Craig C. Brown, Arlington, Tex.

[73] Assignee: Surgikos, Inc., Arlington, Tex.

[21] Appl. No.: 848,663

[22] Filed: Apr. 4, 1986

[51] Int. Cl.⁴ .............................................. A61L 15/00
[52] U.S. Cl. ..................................... 128/156; 424/28
[58] Field of Search ............... 128/156, 334 R, 335.5; 260/123.7; 264/103; 435/69, 273; 424/28

[56] References Cited

U.S. PATENT DOCUMENTS 4,271,070 6/1981 Miyata et al. ........................ 128/156
4,310,509 1/1982 Berglund ................................ 424/28
4,323,557 4/1982 Rosso et al. ........................... 424/28

Primary Examiner—Gregory E. McNeill
Attorney, Agent, or Firm—Michael Q. Tatlow

[57] ABSTRACT

A surgical dressing or incise drape material comprising a substrate coated with an antimicrobial containing adhesive. The antimicrobial is polyhexamethylene biguanide hydrochloride and is distributed in the adhesive as particles having a size of from 20 to 300 microns.

7 Claims, 3 Drawing Figures

ANTIMICROBIAL DRESSING OR DRAPE MATERIAL

FIELD OF THE INVENTION

The present invention relates to surgical dressings and incise drapes which have an adhesive surface to secure the dressing or drape to a patient and in which the adhesive contains a salt of polyhexamethylene biguanide as a broad spectrum antimicrobial agent. A portion of the antimicrobial agent is of a particle or domain size approximately equal to or greater than the thickness of the adhesive.

BACKGROUND OF THE INVENTION

The desirability of incorporating antimicrobial or antibacterial agents into different types of surgical dressings has been evident for some time. Although numerous antimicrobials are available, most of these antimicrobial agents are either not suitable for contact with human skin, or they are very difficult to incorporate into an adhesive composition.

U.S. Pat. No. 3,579,628 discloses a film dressing which contains a composition which reacts with water to generate a bacteriostatic substance.

U.S. Pat. No. 3,983,209 discloses a method of applying an antimicrobial to a wound by incorporating an antimicrobial agent into a bioerodible polymer. The polymer may be incorporated into an absorbent carrier for application to the wound.

U.S. Pat. No. 4,310,509 discloses an adhesive composition which contains a polyvinylpyrrolidone-iodine complex and which is incorporated into a solvent-based adhesive for application to a flexible backing material to be used on human skin. In order to insure that the antimicrobial will be present on the skin-contact surface of the material, the antimicrobial is uniformly dispersed throughout the adhesive layer of the product.

U.S. Pat. No. 4,323,557 discloses a process incorporating a solution of an iodide and iodine into a pressure-sensitive adhesive to be used in contact with human skin.

U.S. Pat. No. 4,340,043 discloses the incorporation of uniform amounts of silver sulfadiazine as an antimicrobial into an adhesive-coated material. The adhesive is a solvent-based adhesive.

The prior art antimicrobial adhesive products mentioned above require that the antimicrobial be uniformly distributed through the entire adhesive. This requirement insures that the antimicrobial will be available on the skin-contact surface of the adhesive when the product is used.

Commonly assigned copending application Ser. No. 707,113 filed Feb. 28, 1985 discloses an antimicrobial dressing in which the antimicrobial, polyhexamethylene biguanide, is in the outer surface of a water based adhesive. This dressing requires the use of a water based adhesive in order to distribute the antimicrobial in the outer surface of the adhesive.

A dressing containing an antimicrobial in a more readily available solvent based adhesive and in which a major portion of the antimicrobial would be available on the skin-contact surface and which would not migrate would be advantageous because less antimicrobial would be required and because there would be greater assurance that the antimicrobial would be present on the skin contact surface of the product when the product was put into use.

SUMMARY OF THE INVENTION

The present invention provides an improved process for manufacturing an antimicrobial containing adhesive dressing and provides an improved dressing in which the antimicrobial is present in the outer, skin-contact portion of the adhesive and will not migrate prior to use.

DETAILED DESCRIPTION OF THE INVENTION

Figure 1:
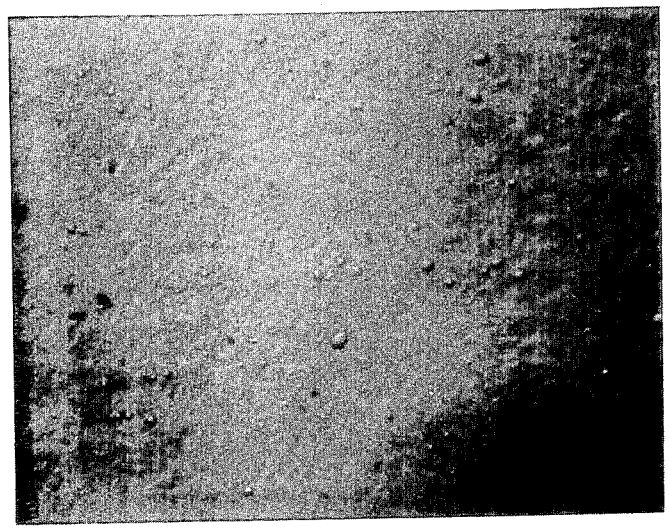
FIG. 1 is a photomicrograph at a magnification of 100× showing the distribution of an antimicrobial in an adhesive.

The present invention is directed to surgical dressings generally and is particularly suitable for dressings which employ substrates which are transparent and which preferably have high moisture vapor transmission rates. Dressings of this type are disclosed in U.S. Pat. No. 3,645,835. The dressings of this type are used for wound dressings as well as for incise drapes. An incise drape is used in a surgical procedure and is applied to the patient at the portion of the body where the surgical incision will be made. The surgical incision is made through the drape material. The presence of an antimicrobial in the adhesive portion of such drape prevents possible contamination of the patient from bacteria that may be present at or near the site of the incision and helps prevent postoperative infection.

The present invention may be used with any substrate normally used for making surgical dressings. The substrate may be a woven or knitted fabric, a nonwoven fabric or a plastic or polymeric film. The substrate that is preferred in the present invention is a polymeric film of polyurethane or of a copolyester which films have moisture vapor transmission rate in excess of 300 grams per square meter, per 24 hours. These films are continuous in that they have no openings in the films, but the moisture vapor transmission character of the films are based on the permeability of the materials to moisture vapor. These films are generally impermeable to liquid water or to other liquids.

The antimicrobial employed in the present invention is polyhexamethylene biguanide hydrochloride. The general formula can be represented as follows:

where n averages 4.5 to 6.5. This material is commercially available as COSMOCIL CQ from ICI Americas Inc. and is referred to therein as PHMB.

The adhesives that are useful in the present invention are generally solvent based skin-contact adhesives that would be compatible with the PHMB. The adhesives may be made with hydrophobic polymers or with mixed hydrophobic and hydrophilic polymers. The preferred adhesive would be an adhesive which exhibits some hydrophilic properties as evidenced by its ability to pick up water. The ability of the adhesive to pick up water will insure that the moisture from the skin of the patient would activate the antimicrobial at the surface or immediately below the surface of the adhesive layer. If a hydrophilic polymer is used which allows water to penetrate the adhesive, the antimicrobial effect can be obtained even if the antimicrobial agent does not extend to the surface of the adhesive.

Typical hydrophobic adhesives that can be used are acrylate polymers such as polymers of 2-ethylhexylacrylate polymerized with a number of different other monomers. Typical of this type of adhesive is Gelva 788 available from Monsanto Chemical Company. Other similar adhesives are copolymers of an acrylate and styrene. Typical of hydropholic polymers are copolymers of isooctylacrylate and n-vinylpyrrolidone in a weight ratio of 85/15. The distinction between hydrophobic polymer and hydrophilic polymer is based on the ability of a sample of the polymer to absorb water in a 24 hour time period at room temperature. The adhesive is weighed, placed in distilled water for 24 hours and re-weighed to determine the amount of water that has been absorbed by the adhesive composition. Hydrophobic polymer will have a water pick-up of less than 1%. The hydrophilic polymers which are preferred in the present invention have a water pick-up of approximately 10%.

The advantage of employing a hydrophillic adhesive over a hydrophobic adhesive is that the concentration of the antimicrobial in the adhesive can be reduced if a hydrophillic adhesive is used. The use of a hydrophillic adhesive allows some penetration of the adhesive by the moisture from the patient's skin which contacts the PHMB and activates the PHMB. The concentration of PHMB in the adhesive can be reduced to less than 1% by weight of the adhesive with the use of a hydrophillic adhesive. A PHMB concentration of 0.5% in a hydrophillic adhesive will be equivalent in effectiveness in killing bacteria as a concentration of 5% in a hydrophobic adhesive. Generally, the antimicrobial adhesive of the present invention contains between 0.2 and 5% by weight, based on the adhesive of PHMB. A hydrophilic adhesive preferably would contain between about 0.2 and 1% by weight of PHMB and a hydropholic adhesive would preferably contain between 3 and 5% by weight of PHMB. In order to produce a product in which a major portion of the antimicrobial will extend through the thickness of the layer of adhesive, the coating levels of the adhesive on the substrate should be such that the thickness of the adhesive layer on the substrate is no greater than about 60 microns. The thickness of the adhesive is between about 30 and 60 microns and preferably between 40 and 50 microns. The adhesive is coated on the substrate at a coating level of approximately 30 to 60 grams per square meter to produce the coating thickness that is desired. The preferred coating level is about 40 to 55 grams per square meter.

In order to insure that the antimicrobial is present in the domains particle spheres of the appropriate size so that the domain or particles of the antimicrobial agent will extend through the thickness of the adhesive it is necessary to exercise considerable care in the introduction of the antimicrobial agent into the adhesive. The PHMB antimicrobial is commercially available as a 20% aqueous solution. If the solution is diluted with additional quantities of water prior to the addition of the adhesive, the domain or particle size of the antimicrobial in the adhesive become too small to effectively extend through the thickness of the adhesive. In addition, if the mixing of the antimicrobial into the adhesive is conducted under very high shear levels, the domain or particle size of the antimicrobial will also be less than the desired diameter. Generally, the procedure for the mixing of the antimicrobial agent is as follows:

The solution of the antimicrobial at a concentration level of 20% in water is introduced into a solvent for the adhesive. In the case of the hydrophilic adhesive mentioned above, the solvent would be ethyl acetate. The antimicrobial is then mixed in with the ethyl acetate at relatively low speed i.e. less than 300 rpm in a mixing vessel which is not baffled and employing a single propeller blade a T-Line laboratory mixer, Model 134-2. After the antimicrobial agent is uniformly mixed with the ethyl acetate, the mixture of ethyl acetate and the antimicrobial is added to the adhesive, again using low shear to uniformly distribute the antimicrobial in the adhesive mixture.

Figure 2:
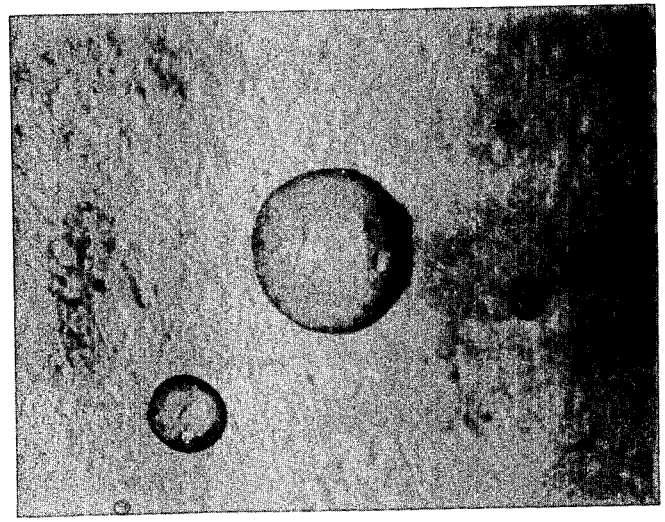
FIG. 2 is a photomicrograph at a magnification of 100× showing the distribution of an antimicrobial in an adhesive in the product of the present invention.

The preferred process of forming the dressing of the present invention is by employing a transfer coating process. In this process, the adhesive containing the PHMB is spread onto a sheet of release paper and dried to remove the solvent. The film or other substrate is then brought under contact with the adhesive and calendered to insure that the adhesive adheres to the film. The product generally will include a release sheet covering the adhesive and the release sheet on which the adhesive is deposited can be used for that purpose or that release sheet can be removed and replaced with another release sheet which is generally a silicone coated paper material. The PHMB is soluble in water. The PHMB forms discrete spheres or domains when mixed with a solvent such as ethyl acetate. The spheres remain discrete when the solvent containing the PHMB is mixed with the adhesive. When the mixture of adhesive and PHMB is dried after coating on the release sheet, the PHMB remains as solid particles or domains in the adhesive. When the substrate is forced into contact with the adhesive and calendered, the larger particles of PHMB are flattened to some extent between the release sheet and the substrate as can be seen in FIG. 2. These flattened particles or domains be at or near the outer surface of the adhesive, i.e., the surface away from substrate, and are readily activated by the moisture on a patient's skin when the dressing or drape is adhered to the patient.

When the adhesive and the antimicrobial agent are mixed under the conditions stated above, i.e., a high concentration of antimicrobial in the aqueous solution and low mixing speeds, the antimicrobial particle size as determined by photomicroscopy, range from about 20 to 300 microns and preferably between 30 and 200 microns and most preferably between 50 and 120 microns. It should be understood that some small portion of the PHMB may be contained in particles of a size less than 20 microns, but the effective amounts of the PHMB will be contained in the particles having a size between the ranges indicated above. The mean particle size would be between about 50 and 80 microns which is thicker than the thickness of the adhesive layer. The median particle size is at least 20 microns and preferably at least 30 microns. The distribution of the antimicrobial in the adhesive is not homogeneous because the relatively large particle containing the antimicrobial are not necessarily uniformly spaced in the adhesive layer on a microscopic basis. However, the distribution is wide enough to insure that in use the antimicrobial will function in the intended manner.

The effect of increasing the water concentration in the PHMB solution added to the solvent and high speed mixing are illustrated in FIG. 1. The PHMB of the sample shown in FIG. 1 was added to the solvent as a 10% aqueous solution. The PHMB and the solvent were mixed in mixer at a speed of 400 RPM. The PHMB in FIG. 1 is dispersed in relatively small particles or domains which are considerably smaller than the thickness of the adhesive layer. These small particles are positioned away from the skin contact surface of the dressing by the adhesive which may prevent moisture from the patients skin from contacting and activating the PHMB.

FIG. 2 is a photomicrograph of the product of the present invention at the same magnification, 100×, as FIG. 1. The PHMB was added to the solvent as a 20% aqueous solution and mixed at 300 RPM. The PHMB is dispersed in much larger particles than the particles in FIG. 1. The larger particles in FIG. 2 have been flattened by the pressure applied when the substrate is forced onto the adhesive layer. The PHMB particles are at or near the skin contact surface of the adhesive and are readily contacted and activated by the moisture on the patient's skin.

The present dressings provide and maintain the activity of the antimicrobial agent over long periods of time, i.e. six hours or more, with sufficient activity to provide adequate biocidal activity and yet the activity is not so great as to cause any problems with potential toxicity. Generally, the release of the antimicrobial, as determined by a saline extraction test, should be at least 20 parts per million and should be less than 145 parts per million to prevent any problem with toxicity or sensitivity of a patient from the antimicrobial.

In the following examples the antimicrobial activity of the particular dressing sample was determined in the following manner. One tenth of a millimeter of each of the test suspensions of particular bacteria in 0.1 percent peptone were applied to the adhesive side of a 2 inch square piece of the dressing which had been placed in a petri dish. The release sheet had been removed from the adhesive. The petri dish is then placed in a high humidity (95%) incubator at 35° C. for the particular exposure times. Controls when used were identical to the treated dressing except for the absence of the bactericidal active ingredient. At the end of the exposure period, 20 ml. of neutralizer solution was added on to the adhesive side of the sample to arrest the action of the bactericidal agent. The neutralized samples were then swirled for ten seconds to release the surviving bacteria from the sample into the neutralizing medium. Surviving bacteria were assessed by standard pourplate technique with trypticase soy agar medium. The colonies were counted to determine the $\log^{10}$ for surviving bacteria after each exposure time.

The saline extraction test is employed to determine the level of the polyhexamethylene biguanide available on the surface of the adhesive. The test method measures the reaction of the PHMB in the extract with sodium hypobromite solutions to produce a yellowish-orange color whose absorbence is measured by visible spectrophotometry at 428 nanometers. Samples of the dressings which are 3.5 inches in diameter are secured to double-sided adhesive tape and attached to the bottom of a petri dish. The release paper on the samples was then removed and 20 millimeters of a 0.9% saline solution at a temperature of 40° C. were placed on top of the sample. The sample was placed in an oven at 40° C. for 30 minutes. The saline was then removed from the sample, mixed with hypobromite and measured at 425 nanometers against the standard solution to determine the level of PHMB.

EXAMPLE I

A series of samples of a bactericidal containing adhesives were prepared. The adhesive employed was a copolymer of isooctylacrylate-n-vinylpyrrolidone in a 85/15 ratio. Four grams of a 20% aqueous solution of PHMB was added to 50 grams of ethyl acetate and stirred with a propeller mixer at 300 rpm for 3 to 4 minutes. The ethyl acetate PHMB mixture was added to 283.4 grams of the adhesive solution at 35% solid and mixed with a propeller mixer at a speed of 300 rpm for 20 minutes. The speed of the mixer was then reduced to 100 rpm. The adhesive containing the PHMB was then coated on a thermoplastic copolyester elastomer film with a reverse roll coater at a coating level of 40 grams per square meter. Each sample contained 0.8% PHMB, weight percent based on the dry adhesive. The domain or particle size of the PHMB was determined from the solution of the adhesive. The saline extract and percent kill at 30 minutes against *S. aureus* was determined. One of the samples, sample D was mixed at a mixing speed of 400 rpm. The results are shown in Table I.

TABLE I

| SAMPLE | ANTIMICROBIAL PARTICLE SIZE RANGE (microns) | MEAN ANTIMICROBIAL PARTICLE SIZE (microns) | SALINE EXTRACTS (ppm) | % kill S. AUREUS 30 minutes |
|---|---|---|---|---|
| A | 20–250 | 80 | 50 | 100 |
| B | 20–90 | 55 | 35 | 100 |
| C | 20–120 | 65 | 40 | 100 |
| D | 0–15 | 10 | <10 | <50 |

The results show that the size of the PHMB particles is reduced by high speed mixing and that the larger particle or domain size of the antimicrobial results in better kill rates of the microorganism.

EXAMPLE II

A series of samples of a bactericidal containing adhesive were prepared as in Example I. In some of the samples, the 20% PHMB was diluted with purified water before mixing with the ethyl acetate. The amount of PHMB solution in the adhesive was varied to result in either 0.4% or 0.8% weight percent based on the dry adhesive. The PHMB was added to the ethyl acetate at low rpm except for sample C which was mixed at 40 rpm. The results are shown in Table II.

TABLE II

| SAMPLE | ANTIMICROBIAL PARTICLE SIZE RANGE (microns) | MEAN ANTIMICROBIAL PARTICLE SIZE (microns) | SALINE EXTRACTS (ppm) | % kill S. AUREUS 30 minutes |
|---|---|---|---|---|
| A 0.4%* 10%** | 0–30 | 15 | <10 | <50 |
| B 0.8%* 10%** | 0–30 | 15 | <10 | <50 |
| C 0.8%* 10%** | 0–15 | 5 | <10 | <50 |
| D 0.4%* 5%** | 10–30 | 20 | <10 | <50 |
| E 0.8%* 20%** | 34–120 | 75 | 45 | 100 |

*Percent PHMB on adhesive
**Percent PHMB in water solution

The results show that the presence of added water reduces the size of the domain or particle of PHMB in the adhesive with the resulting loss of availability of PHMB, (saline extract) and reduction in kill rate.

EXAMPLE III

A series of bactericidal containing adhesives were prepared as in Example I. The adhesives employed were hydrophobic acrylate-type adhesives, Rohm & Haas 969, A in Table III and Galva 788, B in Table III. In order to maintain the desired biocidal activity, 5 percent PHMB as a 20% aqueous solution was added to these adhesive. The adhesives were transfer coated on a substrate as in Example I and the particle size, saline extract and percent kill against *S. aureus* were determined. The results are in Table III.

TABLE III

| SAMPLE | ANTIMICROBIAL PARTICLE SIZE RANGE (microns) | MEAN ANTIMICROBIAL PARTICLE SIZE (microns) | SALINE EXTRACTS (ppm) | % kill S. AUREUS 30 minutes |
|---|---|---|---|---|
| A | 20–90 | 55 | 30 | 99.99 |
| B | 20–100 | 60 | 35 | 99.99 |

EXAMPLE IV

Samples of a dressing containing 0.8% PHMB were prepared as in Example I. The in vitro antimicrobial efficacy of the samples was compared with a commercially available incise drape material containing an iodophor in the adhesive. The efficacy was determined against *Staphylococcus aureus* and *Escherichia coli* at various time periods and is reported as Percent kill in Table IV.

TABLE IV

| | E. coli | | S. aureus | |
|---|---|---|---|---|
| Time in minutes | PHMB Percent kill | Iodophor Percent kill | PHMB Percent kill | Iodophor Percent kill |
| 0 | 0 | 0 | 0 | 0 |
| 1 | 87.2 | 23.5 | 73.6 | 20.0 |
| 2 | 94.4 | 11.8 | 85.2 | 13.3 |
| 5 | 99.6 | 47.0 | 98.8 | 26.7 |
| 10 | 99.99 | 94.1 | 99.98 | 13.3 |
| 30 | 100 | 100 | 100 | 98.7 |

The results show that the PHMB containing product of the present invention gives a more rapid kill of the tested microorganisms.

EXAMPLE V

The test of Example IV was repeated, but the test suspensions of bacteria also contained 5 percent whole defibrinated sheep's blood. The results are shown in Table V.

TABLE V

| | E. coli | | S. aureus | |
|---|---|---|---|---|
| Time in minutes | PHMB Percent kill | Iodophor Percent kill | PHMB Percent kill | Iodophor Percent kill |
| 0 | 0 | 0 | 0 | 0 |
| 1 | 42.1 | 20.6 | 16 | 14.8 |
| 2 | 55.3 | 8.8 | 44 | 29.6 |
| 5 | 71.0 | 17.6 | 76.8 | 37.0 |
| 10 | 84.5 | 14.7 | 79.2 | 22.2 |
| 30 | 99.4 | 5.9 | 97.4 | 22.22 |

The results indicated that the presence of blood inactivates the iodophor to a greater extent than the PHMB.

EXAMPLE VI

An in vivo test comparing the efficacy of the present dressing and the iodophor drape of Example IV was performed in the following manner: Skin on the scapular region of the backs of volunteers was prepped using a 70 percent isopropanol wash for 1–2 minutes. The prepped skin was then seeded with either *Staphylococcus epidermidis* or *Escherichia coli*. Seeded and unseeded areas were then covered with antimicrobial treated incise drape for selected time intervals. At the end of each contact period the surviving bacteria were collected using a cup/washing technique with enumeration of bacteria using standard pourplate procedures with trypticase soy agar medium. As with the in vitro methods, a competitive iodophor-treated incise drape material was included for comparative purposes. The results are shown in Table VI.

TABLE VI

| Time in minutes | E. coli | | S. aureus | |
| --- | --- | --- | --- | --- |
| | PHMB Percent kill | Iodophor Percent kill | PHMB Percent kill | Iodophor Percent kill |
| 0 | 0 | 0 | 0 | 0 |
| 10 | 99.9 | 48.0 | 89.8 | 58.2 |
| 30 | 99.9 | 85.6 | 93.5 | 73.8 |
| 360 | 99.99 | 99.8 | 99.6 | 99.8 |

The results indicate a faster kill rate with the PHMB dressings.

I claim:

1. A surgical dressing comprising a substrate coated on one surface with a solvent based skin contact adhesive, said adhesive having a thickness of from 30 to 60 microns, particles of polyhexamethylene biguanide hydrochloride distributed through the adhesive, said particles having a size of from 20 to 300 microns.

2. The dressing of claim 1 in which the particles have a size of from 30 to 200 microns.

3. The dressing of claim 1 in which the particles have a size of from 50 to 120 microns and a median particle size of at least 20 microns.

4. The dressing of claim 1 in which the particles are in the form of flattened spheres.

5. The dressing of claim 1 in which the adhesive is hydrophilic.

6. The dressing of claim 5 in which the adhesive is a copolymer of isooctylacylate a n-vinylpyrrolidone in a weight ratio of 85/15.

7. A process of forming adhesive coated surgical dressing containing an antimicrobial comprising mixing a 20% aqueous solution of polyhexamethylene biguanide hydrochloride with a solvent which is compatible with the adhesive at a mixing speeding of no more than 300 RRM, adding the mixture to an adhesive, applying the adhesive to a release surface in an amount of from 40 to 55 grams per square meter, drying the adhesive, and applying a substrate for the dressing to the adhesive.

* * * * *